United States Patent [19]

King

[11] Patent Number: 4,573,961
[45] Date of Patent: Mar. 4, 1986

[54] ELECTRONIC CONTROL METHODS FOR PUVAPHERESIS APPARATUS

[75] Inventor: Martin J. King, Largo, Fla.

[73] Assignee: Extracorporeal Medical Specialties, Inc., King of Prussia, Pa.

[21] Appl. No.: 665,831

[22] Filed: Oct. 29, 1984

[51] Int. Cl.$^4$ .......................................... A61M 37/00
[52] U.S. Cl. ....................................................... 604/6
[58] Field of Search .................................... 604/4, 5, 6

[56] References Cited

U.S. PATENT DOCUMENTS 4,398,906  8/1983  Edelson ................................... 604/6
4,458,539  7/1984  Bilstad ................................. 604/6 X Primary Examiner—Harland S. Skogquist
Attorney, Agent, or Firm—Mark A. Hofer

[57] ABSTRACT

Methods are provided for ensuring the safety of a patient undergoing extracorporeal treatment by irradiation of a photoactivatable reagent in contact with the patient's blood including simultaneous digital and analog monitoring of temperature, voltage and current sensor signals. Also provided is a control system for controlling and regulating the various components of the photophoresis patient treatment system.

4 Claims, 6 Drawing Figures

ELECTRONIC CONTROL METHODS FOR PUVAPHERESIS APPARATUS

FIELD OF THE INVENTION

This invention relates to the field of treating cells with photoactivatable compounds and radiation which activates the compound thereby affecting the cells and specifically, relates to clinically useful systems for the extracorporeal treatment of blood cells, especially leukocytes, with UV radiation.

BACKGROUND OF THE INVENTION

It is well-known that a number of human disease states may be characterized by the overproduction of certain types of leukocytes, including lymphocytes, in comparison to other populations of cells which normally comprise whole blood. Excessive or abnormal lymphocyte populations result in numerous adverse effects to patients including the functional impairment of bodily organs, leukocyte mediated autoimmune diseases and leukemia related disorders many of which often ultimately result in fatality.

U.S. Pat. Nos. 4,321,919; 4,398,906; 4,428,744; and 4,464,166 to Edelson describe methods for treating blood whereby the operation or viability of certain cellular populations may be moderated thereby providing relief for these patients. In general, the methods comprise treating the blood with a dissolved photoactivatable drug, such as psoralen, which is capable of forming photoadducts with DNA in the presence of U.V. radiation. It is believed that covalent bonding results between the psoralen and the lymphocyte nucleic acid thereby effecting metabolic inhibition of the thusly treated cells. Following extracorporeal radiation, the cells are returned to the patient where they are thought to be cleared by natural processes but at an accelerated pace believed attributable to disruption of membrane integrity, alteration of DNA within the cell, or the like conditions often associated with substantial loss of cellular effectiveness or viability.

Although a number of photoactivatable compounds in the psoralen class are known, 8-methoxy psoralen is presently the compound of choice. An effective radiation for this compound, and many psoralens in general, is the ultraviolet spectrum in the range of approximately 320 to 400 nanometers, alternatively referred to as the U.V.A. spectrum. As the development of photoactivatable compounds proceeds, it may be expected that changes in the preferred activation radiation spectrum will be necessary. Suitable selection of radiation sources will, of course, increase treatment efficiency and is contemplated as an obvious optimization procedure for use with the inventions disclosed herein.

Although Edelson's methods have been experimentally shown to provide great relief to patients suffering from leukocyte mediated diseases, numerous practical problems remained requiring solutions. In particular, Edelson fails to provide a suitable apparatus for applying radiation to the cells, e.g. via a treatment station, in an economical and efficacious manner, or a system for incorporating a treatment station providing for the treatment of a patient in a clinically acceptable format.

Conventional techniques for photoactivating compounds associated with cells have relied on a plurality of devices including flasks, filtration columns, spectrophotometer cuvettes, and petri dishes. The sample to be irradiated is added to the containers and the container placed adjacent to the radiation source. Such systems tend to be laboratory curiosities as they fail to provide the necessary safeguards intrinsically necessary where patient bodily fluids are concerned, particularly since these fluids must be returned to the patient thereby necessitating strict avoidance of contamination. Further, such methods tend to be volume limited, are characterized by many mechanical manipulations and are generally unacceptable from a clinical and regulatory viewpoint. It is an object of the present invention to provide methods and apparatus suitable for use with the Edelson methods to overcome the limitations associated with the conventional expedients.

Copending application U.S. Serial No. 650,602, of Taylor describes a preferred form of a practical device for coupling the radiation provided by commercially available light sources, such as the so-called "blacklight" fluorescent tubes, to cells for treatment by Edelson's photoactivated drug methods. In summary, the disposable cassette described therein comprises a plurality of fluorescent tube-like light sources such as the U.V.A. emitting Sylvania F8TS/BLB bulb, which are individually, coaxially mounted in tubes of larger diameter which are, in turn, coaxially mounted in sealing arrangement within second outer tubes of even larger diameter thereby forming a structure having two generally elongated, cylindrical cavities about each radiation source. The inner cavity preferably communicates with the atmosphere thereby facilitating cooling of the radiation source. The second tube forming the outer cavity further comprises inlet and outlet means for receiving and discharging, respectively, the cells to be irradiated. A plurality of these structures are "ganged" and suitable connections made between inlets and outlets of adjacent members to provide for serpentine flow of cells through each outer cavity. Thus, continuous flow of the cells through the plurality of cavities surrounding the centrally disposed radiation sources facilitates thorough treatment of the cells. Additional, detailed description of the Taylor device may be obtained by direct reference to the aforesaid application.

To be fully practical, however, the Taylor device requires a clinically acceptable instrument to house the device and to provide the cells to be treated in an appropriate form. It is an object of the present invention to provide such a device.

To date and for clinical use-approval related purposes, the Edelson methods have been performed utilizing a generally impractical and unwieldy apparatus consisting of a large, desk-size metal box containing a series of flexible, relatively transparent plastic bags through which patient blood was pumped. As the blood flowed through each bag, it was irradiated on either side by a plurality of ultraviolet emitting, standard sized, "fluorescent" type tubes housed within the box. Blood flow was generated by means of a separate pump located nearby and connected to the plastic bags as well as source and drain reservoirs by flexible tubing.

Prior to treatment, it has been found preferable to perform leukocyte enriching operations for the purpose of removing substantial portions of red blood cells from the treatment circuit. With the preliminary experimental apparatus, leukocyte enrichment was obtained by centrifuging batch quantities of blood in large volume centrifuge tubes and then dispensing the supernatant plasma into the source bag for treatment. Thus, the Edelson methods have been carried out to date via a cumbersome series of labor intensive, error-prone steps, often exposing the patient's blood to numerous potential sources of contamination during its travels to and from equipment, none of which was designed to optimize the Edelson procedures. Excessive time delays and extensive mechanical manipulations were further exacerbated by the typically divergent locations of various pieces of equipment, necessitated by their space consuming construction. These considerations have resulted in lengthy treatment times and, due to the numerous physical manipulations required, have concommittantly and unacceptably increased the risk of loss or contamination of patient's blood.

It is an object of the present invention to provide methods and apparatus for increasing patient safety thereby also raising his comfort level as well as meeting regulatory acceptability standards.

It is another object of the present invention to provide a complete treatment system which contains all the elements necessary for the withdrawal, separation, and treatment of the patient's blood in a compact and clinically acceptable size and to provide the system in a mobile and automated format thereby reducing the risk of inadvertent contamination while concurrently facilitating the ease with which treatment may be given.

It is still another object of the present invention to provide a suitably automated instrument which can be monitored and operated by less trained personnel thereby lowering treatment costs in accordance with the recently enacted fiscal policies.

It is yet still another object to provide a treatment system suitable for use in the clinical arena whereby the acceptability of the Edelson procedures may be augmented so that a greater number of patients may be meaningfully treated.

BRIEF DESCRIPTION OF THE DRAWINGS

These and still other objects of the invention will become apparant upon study of the accompanying drawings wherein.

SUMMARY OF THE INVENTION

In accordance with the principles and objects of the present invention there are provided methods for electronically controlling the punapheresis system for extracorporeally photoactivating a photoactivatable reagent in contact with blood cells wherein the treatment comprises the steps of collecting and separating on a continuous basis blood from a patient while the patient is connected to the apparatus, returning undesired blood portions obtained during separation, disconnecting the patient from the treatment system while the desired portion is photoactivatably treated whereupon the thusly treated cells are returned to the patient. The patient treatment system under electronic control of the inventions hereof, seeks to broadly maximize a patient's safety as well as optimize procedurally the various aspects of such photoactivation treatment by breaking the entire procedure down into three stages or modes. The apparatus, in the first mode or phase, collects and separates blood on a continuous basis as it is withdrawn from the patient and to return unwanted portions to the patient while the patient remains connected to the apparatus. Thereafter, prior to energizing the irradiation sources for photoactivating the photoactivatable reagent in contact with the desired blood portion, the patient is disconnected from the machine thereby isolating him (or her) physically and electrically from the energizing high voltage, a potential source of harm. Following photoactivation, the treated cells may then be facilely returned to the patient utilizing a variety of techniques, the preferred being a simple drip chamber gravity feed infusion line.

Figure 1:
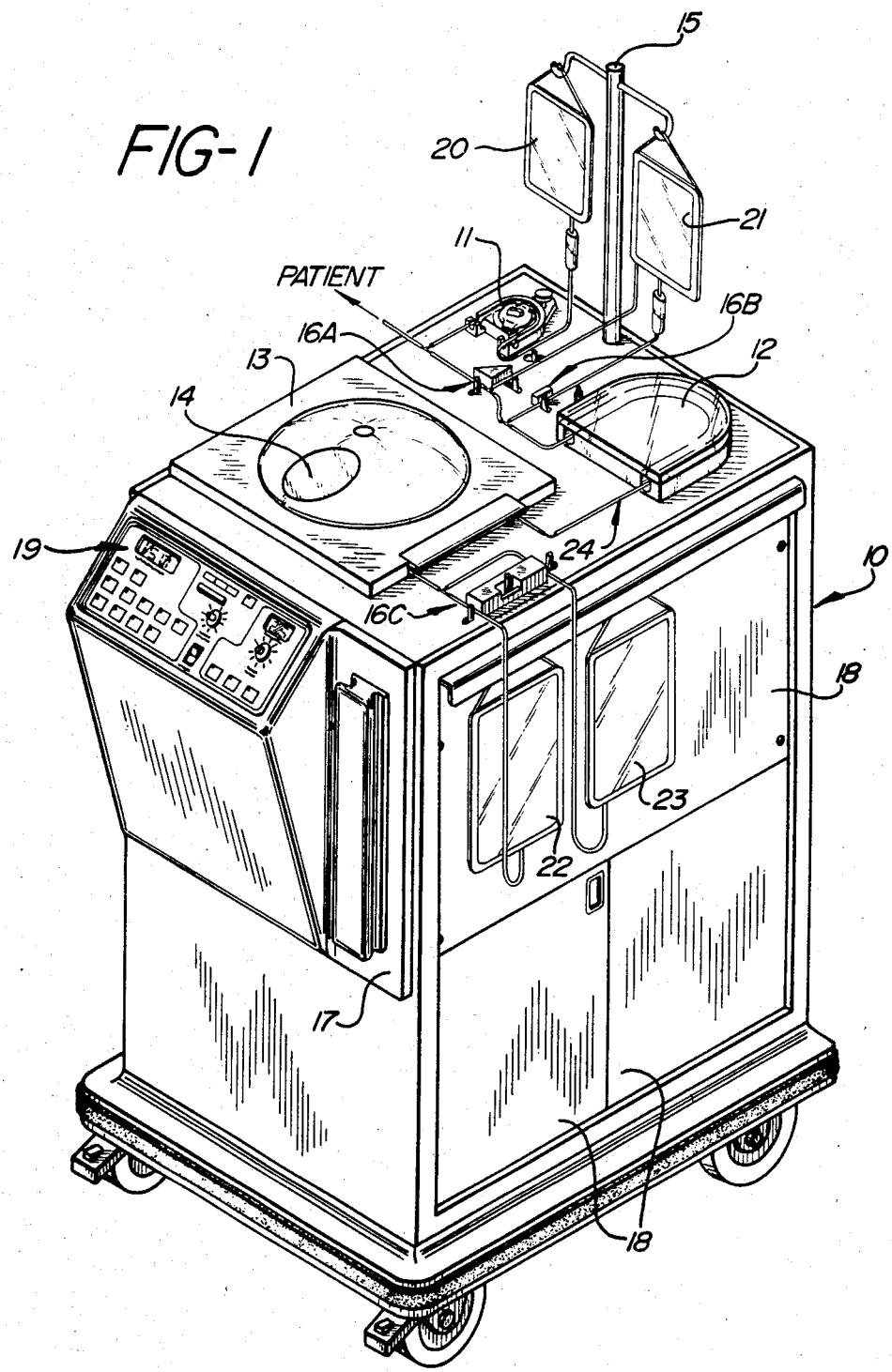
FIG. 1 illustrates a preferred configuration of the system in the collection and separation mode.
Figure 2:
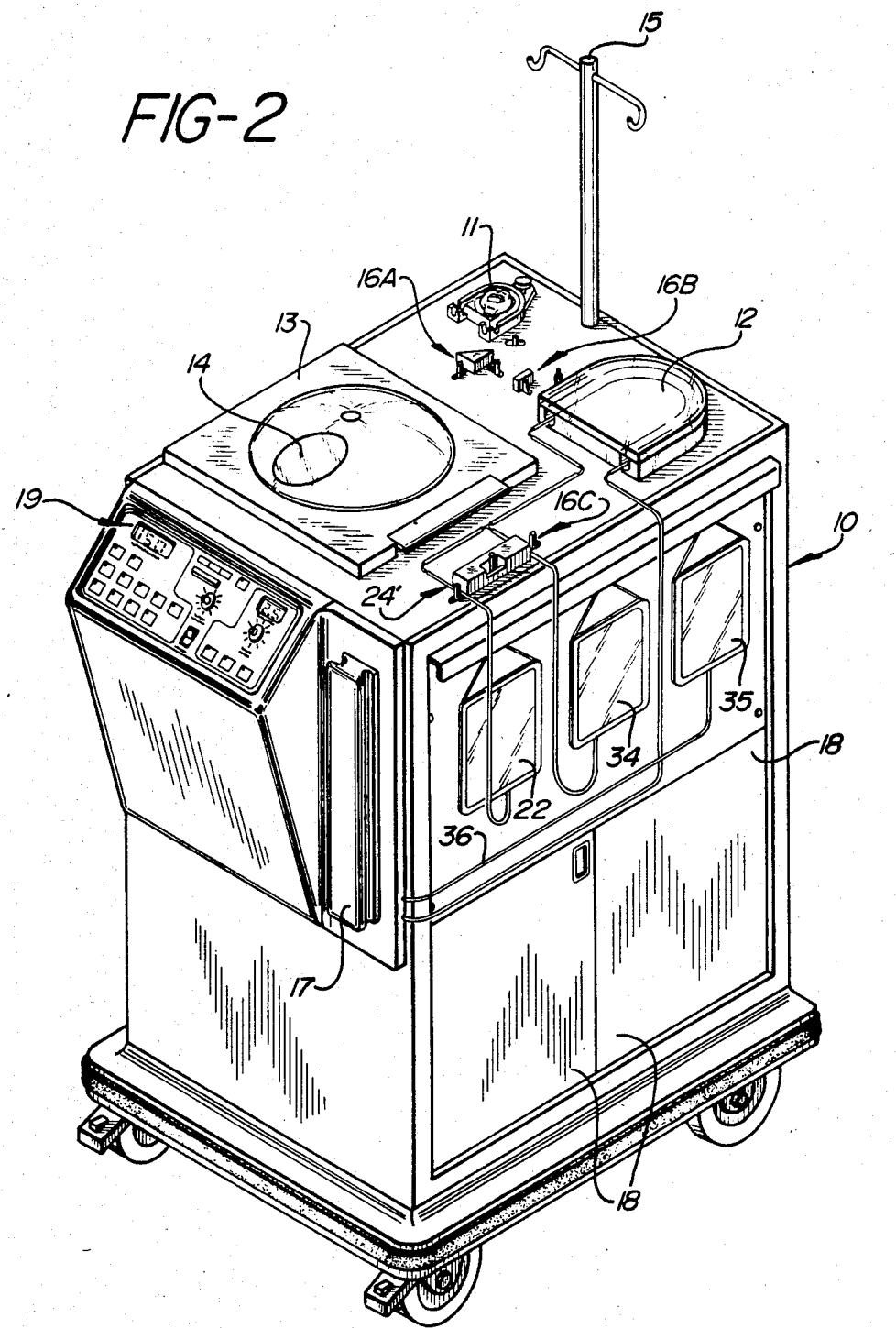
FIG. 2 depicts the system in the treatment mode.
Figure 3:
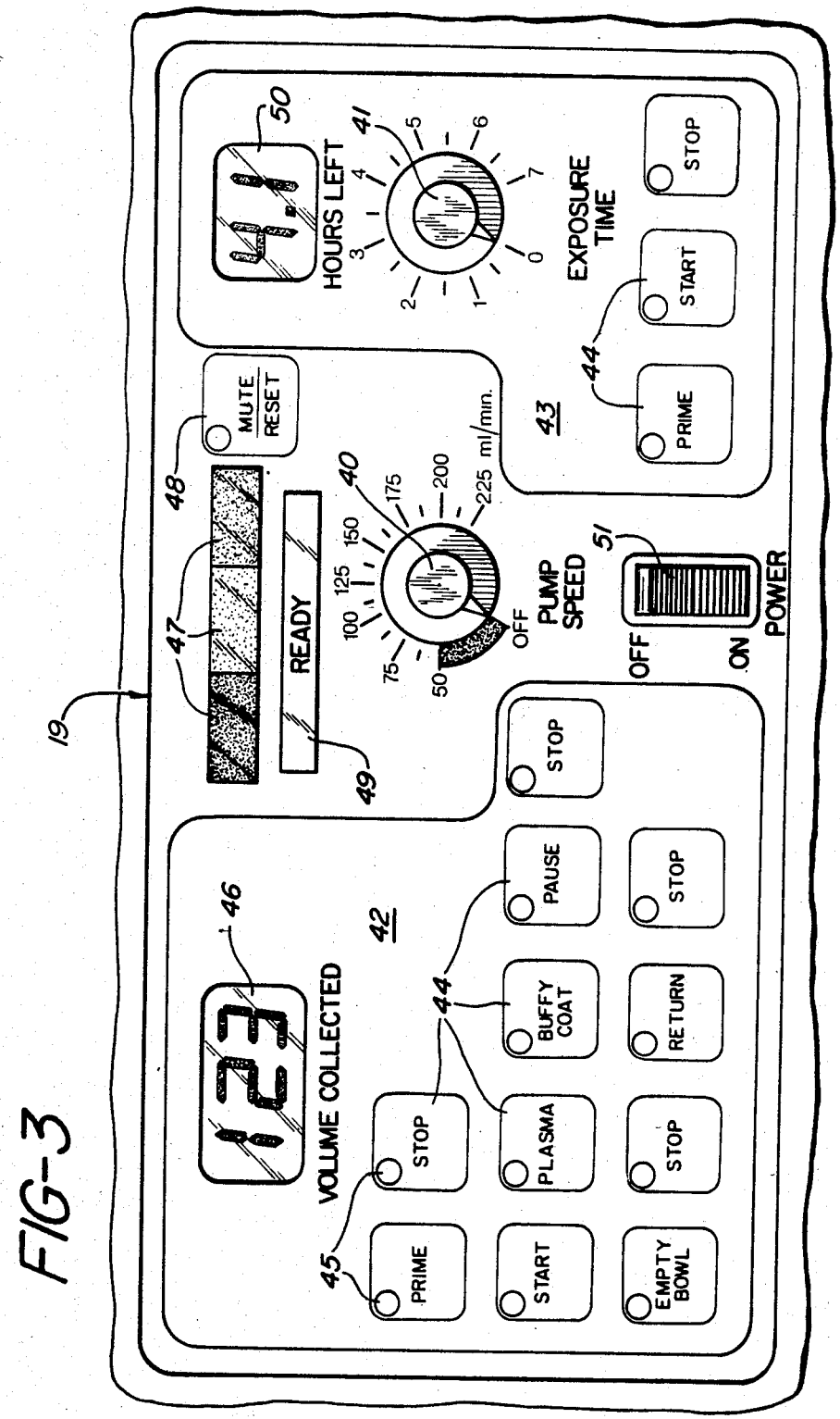
FIG. 3 shows the control panel for the system.

FIGS. 1, 2, and 3 show various aspects of the apparatus developed by the assignee hereof for extracorporeally treating a patient based in part upon the scientific discoveries of Edelson. The design, construction and operation of the apparatus 10 is the result of a number of separate inventions some of which form the subject matter of copending commonly assigned applications including U.S. Ser. No. 665,834 to Goss entile "Three Phase Irradiation Treatment Process"; U.S. Ser. No. 665,832 to King entitled "Automated Photopheresis Blood Portion Control Method"; U.S. Ser. No. 665,827 to Troutner entitled "Valve Apparatus for Photoactivation Patient Treatment System"; U.S. Ser. No. 665,833 to King et al. entitled "Patient Photopheresis Treatment Apparatus & Method"; and U.S. Ser. No. 665,817 to Troutner entitled "Cassette Drawer Assembly for Photoactivation Patient Treatment System", the relevant parts of which are fully incorporated herein by reference.

The operation of the device and performance of the methods can be divided into three basic phases or modes, depicted in part by FIGS. 1 and 2. The first phase is shown substantially in FIG. 1 wherein the patient is connected at the point shown such as by venipuncture methods well-known and developed to a high degree in the dialysis arts. Patient blood, as it flows to the apparatus 10 (alternately referred to herein as the puvopheresis apparatus or system) is preferably infused, under control of pump 11, with an anti-coagulant agent contained in container 20 hung from stand 15. Control of the flow of patient blood to the remainder of apparatus 10 is controlled largely by clamping means 16a which has the dual function of also controlling flow in the reverse direction as well as flow to return container 21; clamp 16a acting as an "or" valve. Normally the blood flows through tubing 24 through blood pump 12 into a continuous centrifuge 13. This continuous centrifuge, available commercially from suppliers such as Dideco and others, is preferably capable of continuously separating blood based on the differing densities of the individual blood components. "Continuously", as used herein means that as blood flows into the centrifuge through line 24, it accumulates within the rotating centrifuge bowl and is separated so that low density components are emitted after a certain minimum volume has been reached within the centrifuge bowl and as additional blood is added. Thus, the continuous centrifuge in effect acts as a hybrid between a pure online system and a pure batch system. This occurs because the centrifuge bowl has a capacity to hold most, if not all, of the most dense portion, typically erythrocytes or red blood cells while emitting lower density portions such as plasma and leukocytes (white blood cells) as whole blood is continuously added. At some point, however, the reservoir volume of the centrifuge is filled with the higher density components and further separation cannot be effectively obtained. Prior to that point, the operator, by viewing the uppermost portion of the centrifuge bowl through magnifying observation point port 14 of the centrifuge cover, can detect qualitatively when the centrifuge emits plasma (as opposed to priming solution), leukocyte enriched portions and non-leukocyte enriched portions such as erythrocytes. Based on the operator's observations, he or she enters through control panel 19 (specifically via panel portion 42) the identification of the individual blood portions as they are emitted from the centrifuge. Based on this information entered by keys 44 (e.g. PLASMA, BUFFY COAT or leukocyte enriched portion) on control panel 19, (shown in FIG. 3) the apparatus 10 controls valve mechanism 16c to direct the leukocyte enriched portion and a predetermined volume of plasma into plasma-leukocyte enriched container 22 while excess plasma, air, priming fluids, erythrocytes etc. are directed to container 23.

Once the centrifuge is no longer capable of further separation due to the attainment of its capacity, the operator directs that the bowl be emptied (see FIG. 3) by suitable data key entry and the contents of container 23 and centrifuge 13 are advantageously pumped into return container 21 by means of pump 12 under the control of valves 16a and c. The foregoing steps may be repeated a number of times or cycles before the desired volume of leukocyte enriched blood and plasma is obtained for further treatment, in each instance the undesired portions being first collected in container 23 and then pumped to return container 21.

Between cycles, the erythrocyte enriched portion which is pumped into return bag 21 is gravity fed back to the patient through a drip infusion operation and controlled by valve 16b. It is preferred that gravity feed be employed rather than pumping the blood back to the patient via pump 12 in order to avoid potential pressurization problems at the infusion insertion site at the patient, and also to avoid foaming or other air related dangers. As may be already appreciated, when initially set up, line 24 may be expected to contain sterilized air which is preferably removed by suitable priming operations utilizing the anti-coagulation agent in container 20; both the air and the priming solution being collected in container 23.

Also to be noted is the predetermination of the desired leukocyte enriched volumes and plasma volume to be collected within container 22 as well as the number of cycles to be employed to collect same. These volumes are selected largely in accordance with the individual volume capacities of the containers as well as the treatment cassette to be described later. Accordingly, these volumes are selected in order to preferably optimize handling efficiency and to ensure patient safety. For instance, one preferred selection would include approximately 250 ml total buffy coat or leukocyte enriched portion and 300 ml of plasma to be collected within container 22. This might require any number of cycles preferably on the order of say three or four bearing in mind that the more cycles that are selected, the lower the total volume of blood withdrawn from the patient at any one time, within minimum capacity limits of the centrifuge bowl, thus increasing the patient's capacity to withstand temporary blood volume depletions and the procedure in general. Alternately, more cycles will also permit more discriminating selection of leukocyte enriched blood as it is emitted from the centrifuge. The buffy coat and plasma volumes as well as the number of cycles are typically physician selected and accordingly, the controls governing the selections are preferably placed within the apparatus 10, such as behind doors 18 where their inadvertent alteration may be avoided especially since no operator interaction is ordinarily required with respect to these data inputs.

Referring now to FIG. 2, a second tubing set for the second operational mode is shown with the leukocyte enriched container 22 connected via tubing line 24' through valve 16c, blood pump 12 to the treatment cassette behind door 17 with a return line 36 to reservoir container 35. The tubing set for the second mode will also preferably include container 34 for providing a priming solution for evacuating air contained within tubing set 24' and the cassette treatment module, described in copending application of Taylor, U.S. Ser. No. 650,602. In brief summary, the Taylor cassette comprises a plurality of ganged cylindrical cavities each of which is concentrically mounted around a cylindrical irradiation source in turn powered by apparatus 10.

In operation, and with respect to FIG. 3, the exposure time on the right hand portion of the panel 43 is set in accordance with physician determined criteria via knob 41. The central control means of the apparatus 10, calculates and displays (50) via central processing unit and memory stored software, the exposure time remaining at the onset of irradiation treatment and as the treatment progresses. Section 43 of the control panel also includes three operator controlled entry data keys 44 whereby the first step, PRIME, may be initiated whereupon the priming solution from container 34 is pumped via blood pump 12 through tubing set 24' and the treatment cassette emptying into reservoir 35. Thereafter, the operator, by pushing START in section 43, initiates actual photoirradiation treatment whereupon the leukocyte enriched portion of the blood collected within container 22 is pumped through tubing set 24' in accordance with suitably altered valve 16c through blood pump 12 to the treatment cassette and return line 36 to reservoir 35.

The treatment cassette container assembly 17 further comprises bubble detectors connected to the central control means for detecting the presence of air about to enter the treatment cassette. The presence of the air indicates the complete evacuation of container 22 and signals the end of the first treatment pass. Thereafter, the central control means reverses the direction of blood pump 12 and draws blood from container 35 back through the treatment cassette through the blood pump and to container 22. The actual direction of the blood flow through the treatment cassette is of no significance as flow in either direction is equally photoactivated. An advantage gained by reversing direction (as opposed to constant cycling in the same direction) is the hydrodynamic mixing of blood as it is passed through the container. Such mixing is thought to result in a more thorough treatment of the individual cells because the statistical probability that each cell will be individually contacted by irradiation is increased. This process of blood flow until container 22 or 35 is emptied and then reversal thereof is continued until the desired exposure time is attained. At that point, the treated blood portion is then preferably returned to blood container 22 and the tubing set 24' discarded. Container 22 is then ideally removed to stand 15 and a third tubing set connected to container 22 for reinfusion of the treated blood portion into the patient. During the second operational mode when the actual irradiation treatment is performed as depicted by FIG. 2, the patient is preferably disconnected from the machine thereby adding to his (or her) comfort level by permitting him freedom to move about but also concommitantly, increasing his safety level as he (or she) is not connected to the machine when the high voltages, necessary to drive the irradiation sources, are present.

To further decrease the risk of contamination to the patient blood and blood portions, each time a connection is made or broken, it is preferably only done once. Thus, container 22 would have three connection points to it; one for the first mode collection of the leukocyte enriched blood portion, one for the second mode treatment phase shown by FIG. 2, and the third for the third operational mode wherein treated blood is reinfused to the patient.

With particular reference to FIG. 3, the control panel 19 of the apparatus 10 is shown with the key board entry buttons 44 each ideally having a light 45 which, when lit, preferably indicates the stage of the operation. As will be noted, the key board entry buttons 44 are preferably placed in sequential order thereby assisting the operator in learning the system and performing the steps in the correct order. Indeed, the central control means will preferably be programmed to prevent out of step sequences from being attempted. Display 46 indicates the volume of leukocyte enriched blood collected in container 22. Although not shown, there is preferably also included a manual override switch contained within apparatus 10 such as behind access doors 18 (see FIGS. 1 and 2) for allowing an experienced operator to select any step out of sequence in the unlikely circumstance that such may be necessary to return all blood to the patient in the event of a machine failure.

The central portion of panel 19 contains power switch 51 as well as blood pump speed control 40 whereby the operator may select the speed with which the blood is withdrawn from the patient and pumped through the system during either collection or treatment phases. Also included in the central section are lights 47. Alphanureric display 49 indicates alarms and status regarding the machine's sequential operations. Status lights 47 are preferably provided in green, yellow, and red colors in order to provide at a glance the overall operating status of apparatus 10. Further included is a mute reset button 48 for quieting an audible alarm activated in the event an alarm condition occurs and operator input is required.

Other features may be readily apparent from the drawings such as the preferable inclusion of casters and caster brakes for enhancing the mobility of the apparatus. Further, upper access door 18 will preferably include mechanical means for assisting in the securement of containers 22, 23, 34, and 35. It may also optionally be outfitted with a transparent or translucent opening in the area beneath container 22 for providing at a glance information regarding the illumination status of the irradiation treatment cassette during the treatment phase. For instance, if the window is of sufficient size, the operator may readily determine that each irradiation source within the treatment cassette is illuminated as desired. Naturally, the material comprising such window is preferably selected in order to contain harmful radiation, if any, within apparatus 10.

Safety of the patient as well as efficiency of operation can be maximized by reducing the operation into three clearly demarcated phases. The first phase, with the patient connected to the apparatus, collects blood from the patient and separates it into the desired leukocyte enriched portion and plasma. The remaining blood portions, essentially erythrocyte enriched, and excess plasma, if any, obtained from the separation processes are then reinfused to the patient. The patient is then disconnected from the apparatus and the tubing set, used during the collection or first phase, discarded with the exception the container 22 having the leukocyte enriched blood portion.

The second phase of the operation then commences with the connection of the irradiation tubing set including the treatment cassette of Taylor or other similar irradiation treatment module. The irradiation tubing set will further preferably contain a reservoir such as container 35 shown in FIG. 2 and in the most preferred embodiment, also container 34 having a priming solution. The leukocyte enriched portion, mixed with a predetermined volume of plasma, is then irradiated in the treatment cassette or other suitable irradiation station until a predetermined level of photoactivation is achieved. The irradiated blood portion is then preferably returned to the original leukocyte container 22 and the second phase terminated upon disconnection of container 22 from the irradiation tubing set. The tubing set is then preferably discarded as it is no longer used in the three phase patient treatment procedure and indeed, is preferably not used again in order to avoid possible interpatient contamination or other sterilization related problems.

The third phase comprises the connection of an infusion tubing set to container 22 for return of the irradiated leukocyte enriched blood portion to the patient. This is preferably accomplished by simple gravity feed such as by the attachment of the container to stand 15 on the apparatus 10 or to any standard I.V. stand as may be suitable and appropriate in the circumstances.

By splitting the process into these three broad phases, a number of unobvious advantages are gained. Foremost among them, is the attainment of patient safety by preventing at all times the possible electrical shock hazard to the patient from the high voltages required for standard irradiation sources. This is prevented because at no time during the first phase, i.e. the only phase during which the patient is connected to the apparatus 10, is there a possible fluid connection between the patient and the irradiation treatment station or cassette. Such a fluid connection (indeed only possible if a leakage should occur in the area of the treatment cassette) with the irradiation electrical power source can only occur during the second phase by which time the patient has already been disconnected from the apparatus. Furthermore, the tubing set complexity is reduced by providing three separate tubing sets for each phase of the operation thereby reducing costs of the tubing set, reducing the difficulty in their manufacture, and reducing the difficulty in their attachment and installation on apparatus 10.

Another unobvious result from dividing the procedure into three phases is the reduction of apparatus complexity in the form of fewer valves and pumps which would otherwise be required. For instance, if one attempted to combine the first and second phases, the resulting complicated tubing set would require multiple pumps and many more additional valves for separately controlling the flow through the centrifuge and the flow through the irradiation treatment station since these could not now be accomplished with a single pump. Complicated tubing sets and numerous pumps and valves greatly increase the risk of breakdowns as well as leakage and contamination to the patient blood thereby undermining the value of the treatment and ultimately dispensing with the objects and principles of the present invention.

Still another problem is solved by the instant invention and this concerns the development of an apparatus and treatment system which may be readily performed by technicians without the need of advanced degrees or other detailed instruction. By breaking the system into three phases, at least two of which are clearly separated on the control panel 19, and the third not requiring the apparatus at all, the technician is more readily capable of grasping the individual sequence of steps and accomplishing the desired irradiation treatment safely, efficaciously, and rapidly. Thus, the complement of personnel capable of performing the photoactivation patient treatment procedures is expanded. It is hoped that this will enhance the acceptability of the Edelson procedures within the clinical environments thereby benefiting more patients.

The three phase process of the instant invention facilitates the design of a patient treatment assembly 10 which has fewer parts, is more easily manufactured and thus available at lower cost, an important criteria in view of recent fiscal constraints placed on the clinical environment. Further, the instant invention allows for simpler tubing sets which in turn may be more readily manufactured and offered at lower cost.

The aforedescribed photopheresis blood treatment apparatus is made largely possible by automated control methods for directing the blood portions derived from the continuous centrifuge into particular containers. The automated method performs in accordance with preset volume determinations which are manually entered pursuant to a physician's direction. These predetermined volumes specify the total volume to be contained within container 22 by setting forth the volume of plasma and the volume of leukocyte enriched blood portion to be collected and directed thereto. Additionally included within these condition setting parameters is preferably the ability to set forth the number of cycles of blood collection and separation required or desired in order to obtain the desired blood volumes.

The actual volumes collected are determined in accordance with the blood volume pumped by the blood pump. This may be suitably monitored and communicated to the central control means by specifically monitoring the speed of the blood pump rotation. Shaft rotation may be conveniently monitored such as by attachment of a slotted disk to the shaft and passage of the slots determined by an optical sensor. The resultant periodic signal may be conveniently correlated with speed of rotation by circuit designs well-known in the art. The rotational speed coupled with the known volume pumping characteristics of the pump, e.g. mls/rotation, will provide the necessary information to permit accurate calculation of the volume of blood pumped.

In actual operation, the ideal procedure would be as follows. The operator primes the tubing set, the blood pump, and the centrifuge with the anti-coagulation solution contained in container 20 via the PRIME button. Thereafter, blood is withdrawn from the patient and pumped by the blood pump into the rotating centrifuge. As the blood enters the centrifuge, it displaces the priming solution which emerges first in accordance with its preferably lighter density. This priming solution is automatically directed into container 23. At some point, the priming solution will be completely displaced from the rotating centrifuge and plasma will begin to emerge. This emergence may be directly observed through port 14 whereupon the operator presses the PLASMA key on control panel section 42. Thereafter, the central control means automatically directs the plasma into container 22 keeping track of the volume as it does so on the basis that the volume being pumped into the continuous centrifuge must equal the volume emerging therefrom. This continues until the operator indicates the leukocyte enriched portion, i.e. buffy coat has begun by pressing the BUFFY COAT entry key whereupon, the leukocyte enriched portion continues to container 22, however, the volume so directed is monitored as buffy coat volume. Alternately, if all of the predetermined plasma volume is collected prior to the emergence of the buffy coat, then the central control means automatically diverts, by valve 16c, the emerging plasma fluid stream to container 23. In that instance, upon the emergence of the buffy coat and the keying of the BUFFY COAT data entry switch 44, the central control means diverts the emerging buffy coat into container 22 again keeping track of its volume.

The collection of the buffy coat will ideally continue in accordance with both the predetermined buffy coat volume as well as the number of collection/separation cycles, also a predetermined condition by the physician. If this most preferred embodiment is employed, then a representative example might be as follows. Assume, that the predetermined volume and cycle conditions are set as follows: 350 mls of plasma, 250 mls of buffy coat, and 5 cycles. In each cycle, the apparatus will collect 250/5 or 50 mls of buffy coat before ending the cycle and thereupon emptying the centrifuge bowl and container 23 and returning the predominantly erythrocytes and perhaps excess plasma to the patient. Prior to the collection of the 50 mls, plasma will emerge from the centrifuge and will be collected in container 22 either until the full 350 mls are collected or, until the buffy coat emerges.

During the next cycle, the central control means will direct the further collection of plasma, if needed, in order to reach the 350 ml predetermined volume and then collect an additional 50 mls of buffy coat. The total volume to be contained within container 22, will then equal 600 mls and would be indicated on display 46 as it is accumulated.

Thus, the apparatus automatically keeps track of the volumes as they are collected thereby facilitating the institution of a convenient number of cycles whereby the removal of large blood volumes from the patient is avoided. Not only is patient safety enhanced thereby, but the automated nature of the procedure eliminates numerous potential sources of error since, in accordance with programming supplied to the central control means, the operator need not attempt to keep track of various plasma and leukocyte enriched volumes collected while still being assured that the final solution for treatment will contain the desired leukocyte concentration based on the predetermined conditions of plasma volume and buffy coat volume.

Figure 4A:
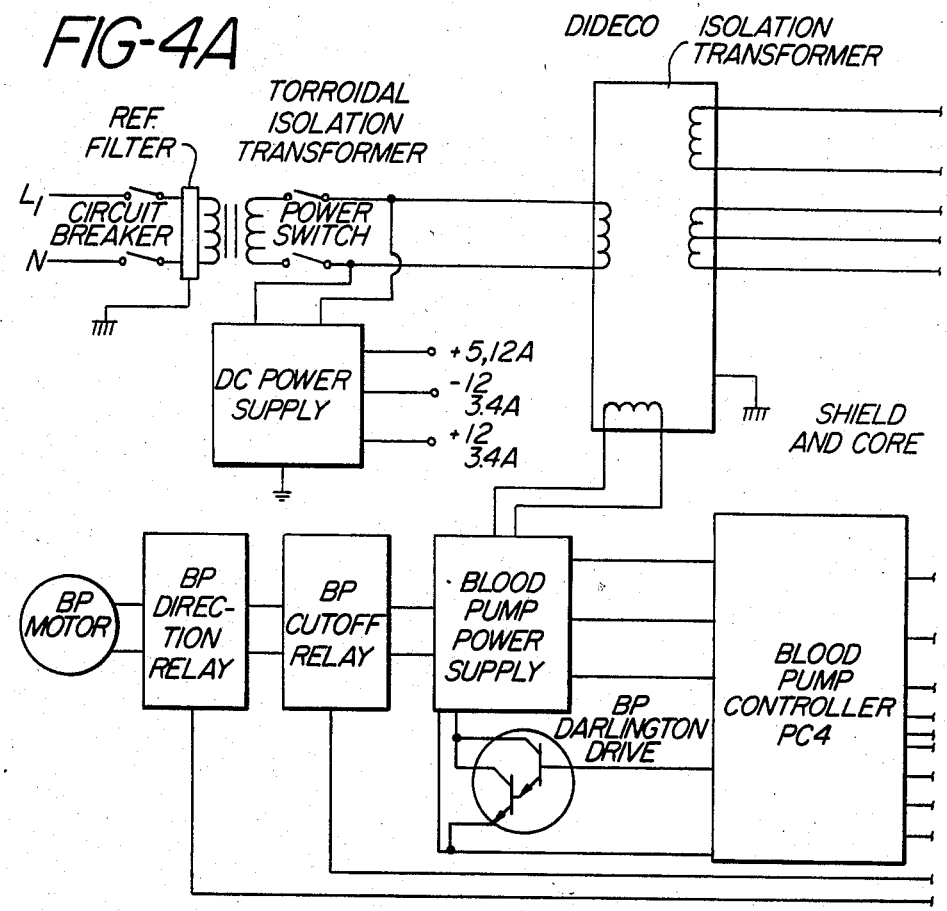
FIGS. 4a, b and c schematically show the preferred electronic control systems for the preferred apparatus.
Figure 4A:
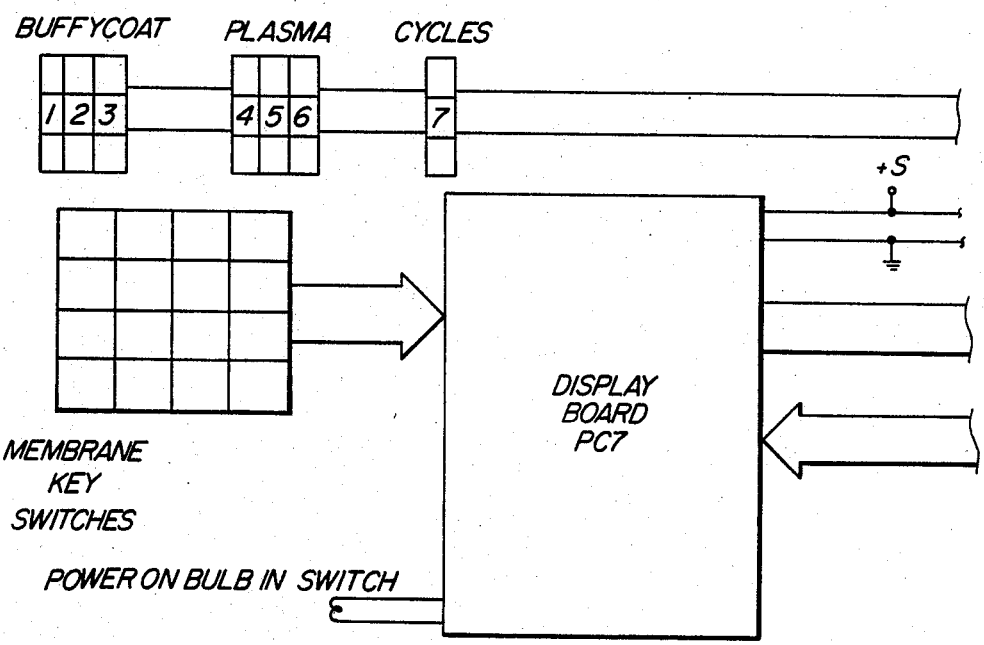
Figure 4B:
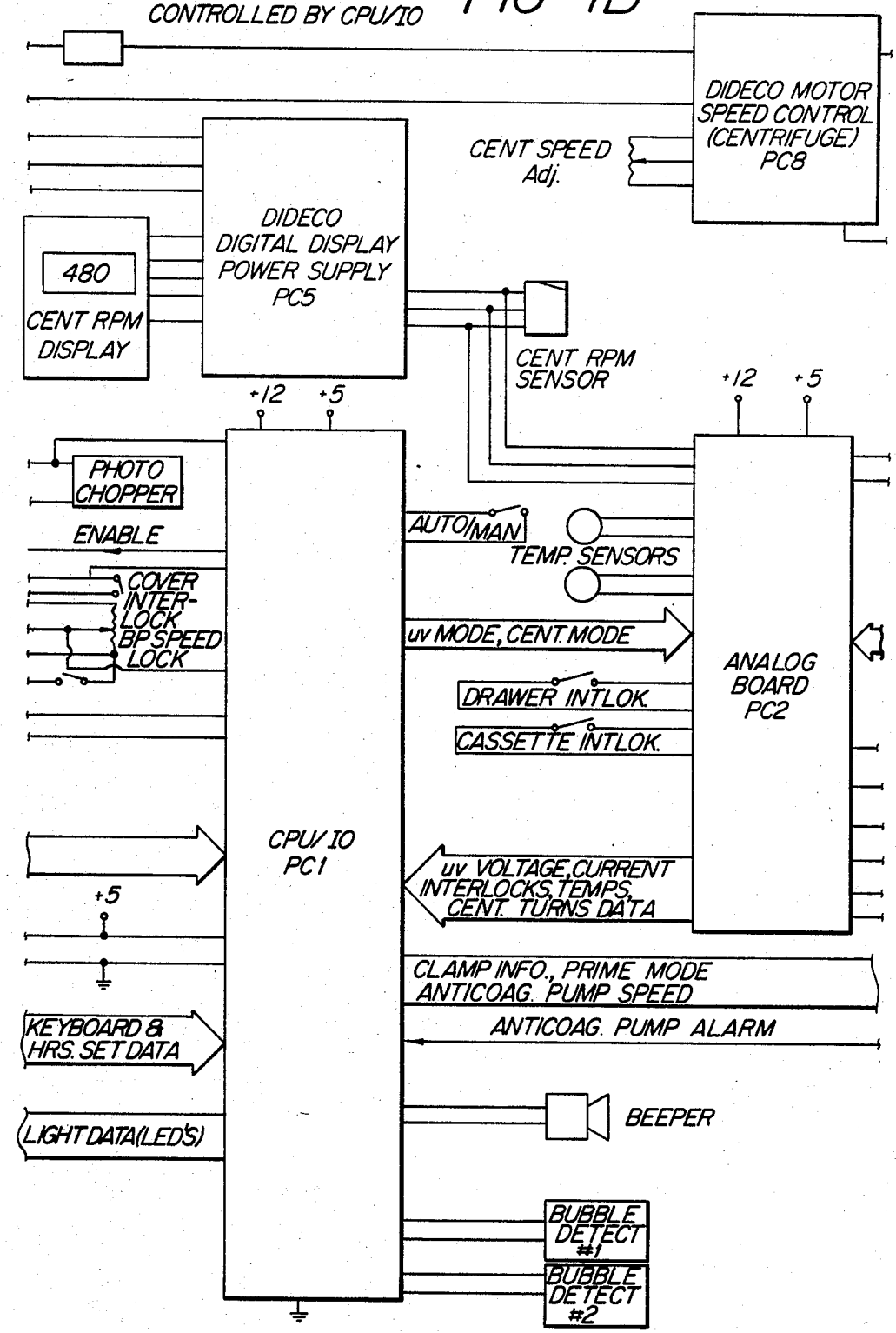
Figure 4C:
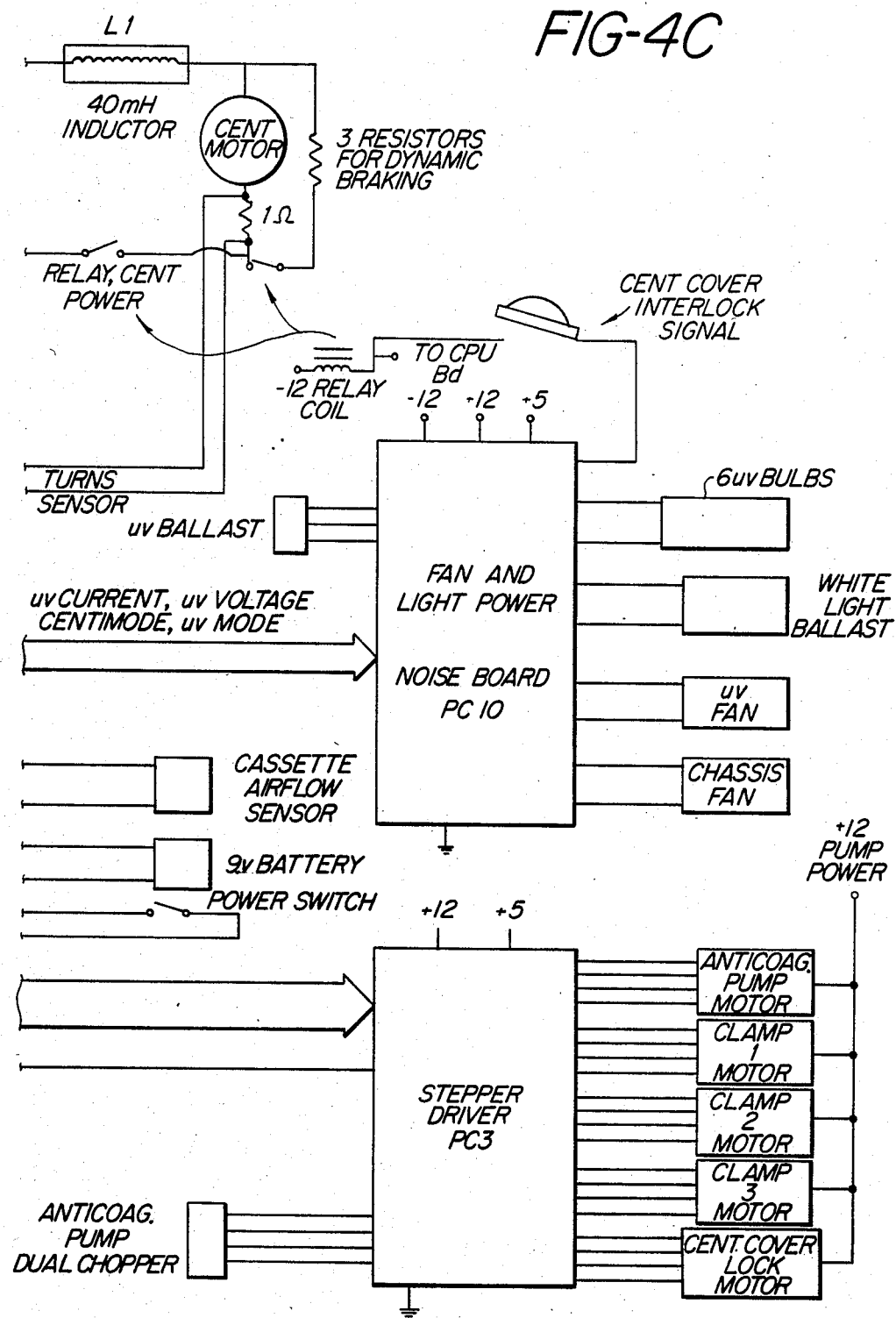

FIGS. 4a, b and c illustrate the preferred control system of the instant invention for controlling and regulating the various aspects of the extracorporeal patient treatment system for the photoactivation of a reagent in contact with the patient's blood. Although a preferred schematic of the control system is shown, it will be readily understood by those skilled in the art that numerous alternatives and rearrangements are possible without departing from the spirit or scope of the present invention. Further, the schematic is presented in block diagram to illustrate the flow of information between the various circuit means and the types of communication being transmitted from one portion of the control system to another, it being readily understood that there are various methods of accomplishing the individual tasks assigned each block diagram, those methods being well within the ken of a reasonably skilled electronics engineer. Accordingly, and since the flow of information is the unobvious aspect, this rather than specific circuit description will be issued, the latter being left as easily implemented by the routineer.

In particular, the figures illustrate the more salient features of the instant invention. Initial energy input is shown at the left uppermost portion of the diagram which energy is ideally fed directly into a torroidal isolation transformer for the express purpose of isolating the patient from the power source. From there, the energy is directed to a DC power supply means for converting the AC voltage and current yielded by the isolation transformer into DC voltages and currents useful in various other portions of the control system. Power is also fed directly to the centrifuge power supply, in this case the centrifuge being obtained from Dideco as a complete unit including its own RPM sensors and digital displays and speed controls. Power is also fed to the blood pump power supply circuit board for powering the blood pump under the control of a blood pump controller. The blood pump controller is in turn connected to the central control means which includes central processor means such as a central processing unit and memory. Various safety interlocks such as the pump cover interlock prevent or enable the blood pump controller from receiving information from the central processing unit and in turn controlling the blood pump through the blood pump power supply circuit. The heart of the system, the central control means includes, in an ideal embodiment, the central processing unit means and memory means for storing preprogrammed instructions or software. Also communicating with the central control means are manual setting means whereby the desired buffy coat volume and the desired plasma volume to be contained within container 22, and the number of cycles used to generate those particular volumes are communicated. Similarly, the data, entered by the operator on the keyboard control panel shown in FIG. 3, is communicated directly with a display circuit and in turn with the central control means. In this manner, the operator is able to identify the blood portion being emitted from the centrifuge and communicate such information to the central control means. The central control means, in response to the inputted data and the preprogrammed instructions, communicates with the driver circuit board for directing the individual servo motors controlling the valves, the anti-coagulation pump speed and the centrifuge cover interlock servo motor for directing the fluids to their respective containers.

Also communicating with the separate driver circuit is the anti-coagulation pump monitor means whereby the speed and direction of the stepper motor controlling the addition of the anti-coagulation reagent is monitored. The central control means further communicates with the analog circuit board whereby information concerning the radiation voltage and current, the various safety interlocks, the temperature monitor signals, and the centrifuge turns data may be exchanged. Thus, the analog circuit board conveys information to the central processing means which allows the latter to monitor safety conditions on a digital basis. Concurrently, the analog circuit board also performs similar safety functions, monitoring the analog signals directly with predetermined thresholds by the use of comparators. In accordance with the safety features of the preferred photopheresis system, the analog circuit means communicates with and controls the power board for energizing the irradiation sources and irradiation source cooling apparati. Finally, the central control means also communicates with bubble detectors associated with the irradiation station whereby decisions may be made regarding the flow of blood through said station. Failure of any of the various safety related signals to meet predetermined thresholds or fall within desired limits, will ideally result in the activation by the central control system of an alarm condition preferably including optical and audible effects. Further understanding and detail may be had by reference to the figures which clearly indicate the flow of information between the various components of the system and the safety features of the present invention.

It will be further understood that numerous alterations may be made, particularly with respect to the features shown in FIGS. 4a, b, and c without departing from either the spirit or scope of the present invention.

What is claimed is:

1. In an extracorporeal patient treatment system for the photoactivation of a reagent in contact with the patient's blood, said system including an anticoagulant infusion pump, a blood pump, a continuous centrifuge for obtaining various blood fractions, containers for receiving said fractions and for returning some fractions to the patient while other fractions are irradiated at an irradiation station, and sensors for generating signals in accordance with blood temperature, irradiation station cooling air flow and irradiation source current and voltage, a method for ensuring the safety of the patient undergoing treatment comprising:

monitoring the temperature of the blood fraction to be irradiated as it enters and as it exits the irradiation station;

further monitoring the flow of cooling air supplied to said irradiation station;

additionally monitoring the current and voltage supplied to the radiation source associated with said irradiation station;

wherein said monitoring is performed on an analog basis whereby said analog signals are individually compared to preset thresholds so that said treatment system may be entirely halted if any of said thresholds is exceeded while, simultaneously, said monitoring is also performed on a digital basis, said sensor signals being converted to a digital basis by analog to digital converter means to enable digital monitoring by a microprocessor in accordance with preprogrammed software criteria communicated to said microprocessor.

2. In an extracorporeal patient treatment system including means for withdrawing blood from said patient, adding an anticoagulation agent to said blood, pumping said blood to a continuous centrifuge for separating from said blood a leukocyte enriched portion having a predetermined volume, returning nonleukocyte enriched blood to the patient, irradiating the leukocyte enriched portion to a preset level of radiation whereby a photoactivatable reagent, in contact with said portion, is activated, and returning the thusly treated portion to said patient, a system for controlling the patient treatment system comprising:

- driver circuit means for controlling (1) valve servo motors for directing blood flow and (2) pump means for adding said anticoagulation agent;
- display circuit means for controlling status display and for receiving blood portion identification input;
- pump circuit means for controlling blood pump means for pumping blood through said patient treatment system;
- analog circuit means for controlling (1) power supply means for said centrifuge and (2) irradiation source and cooling power supply means, and for receiving signals generated by (1) irradiation cooling air flow sensor means, (2) blood temperature sensor means, and (3) centrifuge speed sensor means;
- alarm means for providing a warning if signals from said sensors fail to satisfy predetermined parameters;
- central control means electronically connected to said driver circuit means, said display circuit means, said pump circuit means, said analog circuit means, and said alarm means, said central control means further including memory means for storing programmed instructions and central processing means for regulating said various circuit means and alarm means in accordance with said instructions; and
- power supply means connected to said driver circuit means and said pump circuit means and said analog circuit means for supply power thereto, said power supply means including an isolation transformer for isolating said patient from power supplied to said patient treatment apparatus.

3. The control system set forth in claim 2 wherein said driver circuit means is further connected to monitor means associated with said anticoagulant agent pump means, for detecting the speed and direction of rotation; and further including centrifuge safety interlock means associated with said centrifuge and connected to said central control means and said analog circuit means.

4. The control system set forth in claim 3 further comprising manual setting means for communicating the predetermined volume of leukocyte enriched blood portion and plasma portion desired and number of collection and separation cycles to obtain said desired volumes, said manual setting means connected to said central control means whereby said central processing means regulates said various circuit means in accordance with instructions from said memory means to obtain said desired volume and blood portion for photoactivation.

* * * * *